United States Patent [19]

Citernesi

[11] Patent Number: 5,733,559
[45] Date of Patent: Mar. 31, 1998

[54] CONTROLLED RELEASE INCLUSION SYSTEM OF GLYCOLIC ACID IN β-CYCLO-DEXTRIN AND PROCESS FOR THE ABOVE SYSTEM PREPARATION

[75] Inventor: Ugo Citernesi, Arcore, Italy

[73] Assignee: I.R.A. Istituto Ricerche Applicate S.r.l., Usmate-Velate, Italy

[21] Appl. No.: 659,803

[22] Filed: Jun. 7, 1996

[30] Foreign Application Priority Data

Jun. 9, 1995 [IT] Italy .................................. MI95A1224

[51] Int. Cl.$^6$ ........................................................ A61K 7/00
[52] U.S. Cl. ............................ 424/401; 424/450; 424/451
[58] Field of Search ........................... 424/450, 401, 424/451; 514/54

[56] References Cited

U.S. PATENT DOCUMENTS

| | | | |
|---|---|---|---|
| 4,767,748 | 8/1988 | Ganguly | 514/54 |
| 5,575,987 | 11/1996 | Kamei | 424/451 |

*Primary Examiner*—Thurman K. Page
*Assistant Examiner*—D. Faulkner
*Attorney, Agent, or Firm*—Oblon, Spivak, McClelland, Maier & Neustadt, P.C.

[57] ABSTRACT

Glycolic acid controlled release inclusion complexes comprising glycolic acid and β-cyclodextrin.

9 Claims, No Drawings

CONTROLLED RELEASE INCLUSION SYSTEM OF GLYCOLIC ACID IN β-CYCLODEXTRIN AND PROCESS FOR THE ABOVE SYSTEM PREPARATION

FIELD OF THE INVENTION

The present invention concerns glycolic acid controlled release inclusion systems consisting of a complex between β-cyclodextrin and glycolic acid as active ingredient to be used in the dermatocosmetic and dermatopharmaceutical fields. Some alpha-hydroxy-acids, among which the more simple is glycolic acid, are present in the skin as natural products, as they are commonly synthesized in the normal organism metabolism. Said alpha-hydroxy-acids (shortly referred to as AHA) exhibit specific functions within the horny layer of epidermis in that, besides having a skin hydrating action, they act on the horny layer desquamation processes, by controlling their correct development and avoiding any hyperkeratinization.

As a matter of fact the appearance of a very dehydrated skin is characterized by the thickening of the horny layer, known as hyperkeratinization, which takes place as a consequence of the external layer lower desquamation degree, due to a higher cohesion existing among the corneocytes. Such process determinates the very characteristic external appearance of the dry skin: rough to the touch, poorly elastic, wrinkly in appearance.

There are many molecules controlling the desquamation level in the skin: water, retinoids, alpha-hydroxy-acids, alpha-acetoxy-acids. Among them, the first three promote the desquamation level, whilst alpha-acetoxy-acids, being the alpha-hydroxy-acid natural antagonists, tend to reduce the desquamation level. Desquamation process depends on the bond strength established among corneocytes: a higher level of intercorneocyte cohesion corresponds to a lower desquamation level and vice versa.

SUMMARY OF THE INVENTION

It has been found that by topical administrating 2–5% alpha-hydroxy-acid containing formulation products a horny layer exfoliating and regenerating action is obtained, which is not immediate, but it is apparent after two–three week treatment. Depending on alpha-hydroxy acid concentration, different effects are obtained: at lower concentrations only the hydrating and plasticizing effects are obtained whilst at higher concentrations the separation-exfoliating effect takes place.

However it is also well known that glycolic acid, as well as other alpha-hydroxy acids, has a skin irritating effect, therefore its high concentration administration to reach the sought effects is very problematic.

It is an object of the present invention a glycolic acid inclusion complex that allows to enhance the active ingredient effectiveness while reducing its irritating index.

It is a further object of the present invention a process for the manufacture of the above inclusion complexes.

It is another object of the present invention the use of said inclusion complexes for the cosmetic or dermato-therapeutic formulation.

These and other objects can be obtained according to the present invention providing for the manufacture of glycolic acid/β cyclo-dextrin inclusion complexes.

Cyclo-dextrin are cyclic oligosaccharides deriving from starch degradation by means of the cyclodextrin-glucosiltransferase an enzyme produced by various microorganisms.

It has been found that by reacting glycolic acid with β-cyclo-dextrin inclusion complexes are formed which provide for a glycolic acid gradual release.

Such glycolic acid controlled release not only increases its bioavailability in time but being the free form glycolic acid only gradually available its irritating action is reduced.

DETAILED DESCRIPTION OF THE INVENTION

The preparation of the inclusion complex may be accomplished by contacting cyclodextrin and an aqueous solution of glycolic acid, and removing the excess water. Preferably the inclusion complex is prepared by melting the desired amount of glycolic acid then adding gradually the β-cyclodextrin under stirring and at such temperature to maintain the mixture in liquid state.

The reaction temperature in such a case is advantageously comprised between 70° C. and 120° C. degrees. Preferably the temperature is kept at 80°–90° C. The behaviour of the glycolic acid present into the cyclodextrin complex has two effects: firstly glycolic acid availability is prolonged in time and therefore its effectiveness is remarkably increased, secondly glycolic acid is always present at low concentration providing for a lower irritating effect of the product.

On the other hand cyclo-dextrins are pharmaceutical and cosmetic accepted products and the complex formation with glycolic acid does not alter in any way the glycolic acid dermatologic properties other then reducing its irritating effect. The β-cydodextrin/glycolic acid inclusion complex may advantageously contain 10 to 50% of glycolic acid.

The inclusion complex according to the invention may be formulated in form of cream, ointment, lotion a. s. o. and in addition it may contain pharmaceutical and cosmetic acceptable eccipients.

Preferably the glycolic acid concentration in the cosmetic formulation may range from 1.5 to 10%, in the dermatologic field the complex can be used as such. The product has the appearance of a water soluble viscous liquid, particularly able to be formulated with the conventional formulation methods well known to the experts in the art.

The following examples illustrates preparation and use of β-cyclodextrin/glycolic acid inclusion complex with a 50% glycolic acid concentration, but it are not intended to limit the scope of the present invention.

Complex Preparation

EXAMPLE 1

70 g of glycolic acid in a 70% aqueous solution was mixed with 49 g powder β-cyclodextrin at room temperature. The mixture was subject to energetic stirring to obtain a homogeneous viscous liquid. The above product was heated to 70°–80° C. and kept under stirring at said temperature up to a complete water evaporation. 98 g of a product was obtained consisting of 50% glycolic acid.

EXAMPLE 2

50 g of glycolic acid was heated up to 80° C. until melting of the product in a round flask equipped with mechanical stirrer. Keeping the melted product under vigorous stirring cyclodextrin (50 g) was added thereto in a period of 30 minutes. The mixture was kept under stirring for a period of 10 minutes, then it was gradually cooled down to room temperature.

Thermal differential analysis of the product obtained under a) and b) shows that a complex was obtained having a melting point different from the ones of cyclodextrin and glycolic acid.

Assessment of the efficacy and of the cutaneous tolerability of the β-cyclodextrin complex of glycolic acid (CCAG) compared with free glycolic acid (AG)

Test of cutaneous tolerability

Two series of tests were carried out to assess the index of cutaneous irritation of free glycolic acid compared with the CCGA complex of glycolic acid 50%, at various concentrations.

The first series of tests consisted in the test of cutaneous irritation or epicutaneous test (Patch Test) by means of occlusive application.

For the second series of tests cutaneous irritation was determined following non-occlusive applications.

Patch-test
Material
  Free glycolic acid 70% (AG)—Du Pont
  50% (CCAG)—prepared according the example 2 above
Samples The samples of AG and of 50% CCAG were applied as water solution at standard concentrations of 5% and 10%.
Selection of Volunteers Ten healthy subjects were selected, of both sex, with negative anamnesis for allergic dermatitis by contact (DAC) and without any other pathology in process during the execution of the Test.
Material used for the Application of the Samples The ready to use plasters for dermoreactions used for the Patch Test were made of white "non woven fabric" with a dermatophilic mass of acrylic adhesive, in the shape of 1 cm diameter disc, covered by small squares of polyethylene.
Mode of Execution The test was performed as follows: after cleansing with 70% alcoholic solution (denatured ethyl alcohol the cutaneous area to be treated (volar surfaces of the forearm), occlusive applications of the substance under examination were carried out for one hour. After that period, the plasters were removed and 15 minutes later the cutaneous reaction was evaluated and classified on the basis of an arbitrary scale.
Cutaneous Reactions Considered The cutaneous reactions considered were:
  erythema
  edema
  exfoliation
  vesiculation
Criteria of Assessment According to the arbitrary scale used for the classification of the cutaneous reactions, 0 corresponds to the absence of reaction, 1 point to a light degree, 2 points to a moderate degree of reaction and 3 points to a reaction of serious gravity.
Evaluation of the Results For each volunteer scores were recorded for each parameter and the mean value was calculated. The sum of four average values (one per parameter) corresponds to the average index of cutaneous irritation (IIM).
Results The products tested were classified on the basis of the average index of cutaneous irritation (II M), reported in table 1.

TABLE 1 classification of the products tested on the basis of the correspondent IIM.

| Average index of cutaneous irritation (IIM) | Classification of the products |
|---|---|
| 0,5 | Non irritating |
| 0,5–2 | Slightly irritating |
| 2–5 | Moderately irritating |
| 5–8 | Very irritating |

On the basis of the average of indices of cutaneous irritation obtained both free (AG) and 50% CCGA resulted NON IRRITATING. However, the average index of cutaneous irritation of free glycolic acid resulted, at comparable concentrations, slightly higher compared to that of glycolic acid complexed with cyclodextrins.

At 10% concentration, free glycolic acid resulted SLIGHTLY IRRITATING, while the glycolic acid complex with cyclodextrins resulted NON IRRITATING. At such concentration therefore AG showed an average index of cutaneous irritation significantly and appreciably higher compared to that of CCAG.

At the two concentrations tested, for both products, there was no evidence of allergic reaction.

TABLE 2 average indices of cutaneous irritation (M) of the products tested and their classification.

| Products tested | IIM | Classification |
|---|---|---|
| AG (col 5%) | 0,2 | Non irritating |
| CCAG (sol. 5%) | 0,1 | Non irritating |
| AG (sol. 10%) | 0,6 | Slightly irritating |
| CCAG (sol. 10%) | 0,1 | Non irritating |

Non occlusive application
Material
  Free glycolic acid 70% (AG)—Du Pont
  50% (CCAG)—prepared according to example 2
Preparation of the Samples The samples of AG 50% CCAG were applied directly on the skin at 50% concentration, pH 2,5 (in $NH_4OH$).
Selection of Volunteers Eight healthy volumary women were chosen, aged between 30 and 50 (average age 37,5).
Mode of Execution The samples were applied on one half of the face (periocular and zygomatic zone) using a badger brush. The duration of the application was decided according to the type of skin and to the cutaneous reaction of the individual volunteer. 5 applications were carried out, one every three or more days according to the subjects.

The irritating effect was assessed before the application and one hour after the application.
Cutaneous Reactions Considered The parameters considered to clinically evaluate the irritating degree of the substance under examination were the following:
  no irritative reaction
  irritative symptoms: erythema, pruritus, burning, desquamation, blistering, eczematous reaction.
Criteria of Assessment The irritating effect was assessed on the basis of an arbitrary scale, based on clinical experience, recorded as follows:
  0=No irritative reaction
  1=Modest reaction (slight reddening, pruritus)
  2=Irritative reaction (erythema, pruritus, desquamation)
  3=Strong irritative reaction (erythema, burning, strong pruritus, desquamation, and more)
Evaluation of the Results After every application the cutaneous reactions of each volunteer were evaluated and a relative score was given.
Results There were no cases of irritation or sensitivity noted in any of the 8 subjects on the left side periocular and zygomatic areas of skin treated with 50% CCAG.

On the right side periocular and zygomatic area of skin treated with free glycolic acid (AG) 2 cases of irritation of average gravity were found after the third application, resolved with the use of topical moisturizer and reduction in the time of application, and one case of average to serious irritation after the second application which required the suspension of the treatment with AG (but not with CCAG on the cutis area of the left side of the face) and the use of topical steroids. No subject tolerated the product for more than three minutes.

TABLE 3

Tolerability test of free glycolic acid (AG) and of its complex with cyclodextrins (CCAG) on 8 volunteer subjects

| no applications applic. time (min) | RIGHT SIDE OF FACE (AG) | | | | | LEFT SIDE OF FACE (CCAG) | | | | |
|---|---|---|---|---|---|---|---|---|---|---|
| | 1a 1 min | 2a 2 min | 3a 3 min | 4a 3 min | 5a 3 min | 1a 1 min | 2a 2 min | 3a 3 min | 4a 4 min | 5a 5 min |
| SUBJECT 1 | 0 | 2/3* | // | // | // | 0 | 0 | 0 | 0 | 0 |
| SUBJECT 2 | 0 | 0 | 2 | 0 | 0 | 0 | 0 | 0 | 0 | 0 |
| SUBJECT 3 | 0 | 0 | 2 | 0 | 0 | 0 | 0 | 0 | 0 | 0 |
| SUBJECT 4 | 0 | 0 | 0 | 0 | 0 | 0 | 0 | 0 | 0 | 0 |
| SUBJECT 5 | 0 | 0 | 0 | 0 | 0 | 0 | 0 | 0 | 0 | 0 |
| SUBJECT 6 | 0 | 0 | 0 | 0 | 0 | 0 | 0 | 0 | 0 | 0 |
| SUBJECT 7 | 0 | 0 | 0 | 0 | 0 | 0 | 0 | 0 | 0 | 0 |
| SUBJECT 8 | 0 | 0 | 0 | 0 | 0 | 0 | 0 | 0 | 0 | 0 |

*Subject 1 had to suspend treatment at the second application because of average to serious irritation.

As is seen in table 3, AG and CCAG had different effects on the subjects tested. All the subjects tolerated CCAG even for 5 minute applications, while the same subjects did not tolerate AG for more than 3 minutes. Also CCAG did not cause any irritation whatsoever, while for AG there were 3 cases of irritation of grade 2 and 2/3.

I claim:

1. Glycolic acid controlled release inclusion complexes comprising glycolic acid and β-cyclodextrin.

2. Inclusion complexes according to claim 1 characterized in that glycolic acid content is comprised between 10 to 50%.

3. Inclusion complexes according to claim 2 characterized in that the glycolic acid content is 50%.

4. Cosmetic composition containing glycolic acid in form of a controlled release inclusion complex with β-cyclodextrin.

5. Cosmetic composition according to claim 4, characterized in that glycolic acid concentration is comprised between 0.5 and 10%.

6. Process for the manufacture of glycolic acid/β-cyclodextrin inclusion complexes characterized in that glycolic acid is reacted with β-cyclo-dextrin.

7. Process according to claim 6, characterized in that glycolic acid is in form of an aqueous solution and water is removed by evaporation to recover the complex in anhydrous form.

8. Process according to claim 6, characterized in that glycolic acid is in melted form and cyclodextrin is gradually added thereto.

9. Process according to claim 8, characterized in that the reaction takes place at a temperature in range of 70° to 120° C.

* * * * *